(12) United States Patent
Li et al.

(10) Patent No.: US 11,871,932 B2
(45) Date of Patent: Jan. 16, 2024

(54) OCCLUSION DEVICE

(71) Applicant: LIFETECH SCIENTIFIC (SHENZHEN) CO., LTD., Guangdong (CN)

(72) Inventors: Anning Li, Shenzhen (CN); Jianyong Liu, Shenzhen (CN)

(73) Assignee: LIFETECH SCIENTIFIC (SHENZHEN) CO., LTD., Shenzhen (CN)

( * ) Notice: Subject to any disclaimer, the term of this patent is extended or adjusted under 35 U.S.C. 154(b) by 0 days.

(21) Appl. No.: 17/619,111

(22) PCT Filed: Jun. 29, 2020

(86) PCT No.: PCT/CN2020/099012
§ 371 (c)(1),
(2) Date: Dec. 14, 2021

(87) PCT Pub. No.: WO2020/259710
PCT Pub. Date: Dec. 30, 2020

(65) Prior Publication Data
US 2022/0257259 A1 Aug. 18, 2022

(30) Foreign Application Priority Data
Jun. 28, 2019 (CN) .......................... 201910579951.1

(51) Int. Cl.
*A61B 17/12* (2006.01)

(52) U.S. Cl.
CPC .. *A61B 17/12122* (2013.01); *A61B 17/12031* (2013.01)

(58) Field of Classification Search
CPC ........ A61B 17/12031; A61B 17/12036; A61B 17/12022; A61B 17/12027; A61B 17/12122; A61B 17/12154
See application file for complete search history.

(56) References Cited

U.S. PATENT DOCUMENTS 6,174,322 B1 * 1/2001 Schneidt .......... A61B 17/12172
606/213
2007/0227544 A1 10/2007 Swann et al.
(Continued)

FOREIGN PATENT DOCUMENTS

CN 102805654 A 12/2012
CN 103598902 A 2/2014
(Continued)

OTHER PUBLICATIONS

International Search Report dated Sep. 28, 2020 in corresponding International Application No. PCT/CN2020/099012; 5 pages.
(Continued)

*Primary Examiner* — Sarah A Long
*Assistant Examiner* — Raihan R Khandker
(74) *Attorney, Agent, or Firm* — Maier & Maier, PLLC (57) ABSTRACT

An occlusion device includes a sealing disc, and a fixing frame connected to the sealing disc and located on one side of the sealing disc. The fixing frame includes a connecting portion connected to the sealing disc and at least one supporting body. The at least one supporting body radiates from the connecting portion and extends towards a proximal end to form a plurality of supporting sections. The supporting section is provided with at least one first restraint portion. The fixing frame is provided with at least one second restraint portion. The occlusion device further includes at least one restraint member. The restraint member is connected to the first and second restraint portion so a portion of the restraint member between the first and second restraint portion generates a restraint force that restrains movement of at least the supporting section.

19 Claims, 7 Drawing Sheets

(56) References Cited

U.S. PATENT DOCUMENTS

| | | | |
|---|---|---|---|
| 2011/0054515 A1* | 3/2011 | Bridgeman | A61B 17/12122 |
| | | | 606/200 |
| 2013/0218193 A1* | 8/2013 | Erzberger | A61B 17/12122 |
| | | | 606/200 |
| 2016/0066922 A1 | 3/2016 | Bridgeman et al. | |
| 2016/0287261 A1* | 10/2016 | Li | A61B 17/12122 |
| 2019/0374229 A1* | 12/2019 | Anderson | A61B 17/12031 |

FOREIGN PATENT DOCUMENTS

| | | | |
|---|---|---|---|
| CN | 105792780 A | 7/2016 | |
| CN | 106923884 A | 7/2017 | |
| CN | 108420469 A | 8/2018 | |
| CN | 109464173 A | 3/2019 | |

OTHER PUBLICATIONS

Office Action dated Mar. 16, 2020, in connection with corresponding Chinese Application No. 201910579951.1 (12 pp., including machine-generated English translation).

Notification to Grant Patent dated Sep. 28, 2020, in connection with corresponding Chinese Application No. 201910579951.1 (3 pp., including machine-generated English translation).

* cited by examiner

OCCLUSION DEVICE

TECHNICAL FIELD

The embodiments relate to the field of interventional medical instruments, and, more particularly, relate to an occlusion device for occluding an internal opening of a human body or an animal body.

BACKGROUND

A left atrial appendage occluder, an atrial septal defect occluder, an aneurysm occluder and other occlusion devices are more and more trusted by doctors and patients because of their structures to achieve excellent occlusion and few life-threatening complications after implantation into a patient's body. In particular, an occluder with an umbrella-shaped fixing frame, such as a cantilever-type occluder, provided with the suspending portions of the supporting rods, such as supporting section portions, there are not restrained mutually, therefore, it is configured to a better adapt to parts to be occluded with different structures in the body.

However, since the suspending portions of the supporting rods are not restrained mutually, using a left atrial appendage occlusion as an example, after a left atrial appendage occluder is implanted into a body, an angle of outward opening of a portion of supporting sections is too large due to the influence of the structure of an inner cavity of the left atrial appendage and the comb muscle, the supporting rods can't be effectively attached to the inner wall of the left atrial appendage, and the tail ends of the supporting sections may be in contact with the inner wall of the left atrial appendage. Therefore, in the beating process of the heart, the inner wall of the left atrial appendage may be damaged due to mutual friction, so that the operation risk of pericardial effusion or even perforating the inner wall of the left atrial appendage is caused.

In addition, the fixing frame, which is woven and heat-set into an umbrella-shaped woven mesh by weaving wires, has an open proximal end after heat-setting, and is supported for fixing by a supporting body portion (i.e., a supporting section) located near the open proximal end. In the release process of the occluder with such a fixing frame, a portion of the supporting sections of the fixing frame are excessively opened outwards to affect the fixation of the fixing frame in the body, and certain operation risks are also caused.

SUMMARY

Therefore, a new occlusion device is needed to solve the problem that a portion of supporting sections are excessively opened outwards when the existing umbrella-shaped occlusion device is implanted into a body.

An embodiment provides an occlusion device which includes a sealing disc, and a fixing frame connected to the sealing disc and located on one side of the sealing disc. The fixing frame includes a connecting portion connected to the sealing disc and at least one supporting body, the at least one supporting body radiates from the connecting portion and extends towards a proximal end to form a plurality of supporting sections, each supporting section is provided with at least one first restraint portion, and the fixing frame is provided with at least one second restraint portion. The occlusion device further includes at least one restraint member which is connected to the first restraint portion and the second restraint portion such that when a portion of the restraint member between the first restraint portion and the second restraint portion generates a restraint force, the restraint force restrains at least movement of the supporting section where the first restraint portion is located in a direction away from the fixing frame.

In one example, a supporting body provided with the first restraint portion is the same as or different from a supporting body provided with the second restraint portion.

In one example, at least one of the first restraint portions and at least one of the second restraint portions are provided on different supporting sections, respectively.

In one example, at least one of the supporting sections is provided with at least one anchor towards the sealing disc, a root of the anchor being fixedly connected to the supporting section, and at least one of the first restraint portions and/or at least one of the second restraint portions being provided on the supporting section within the range of 0.1 mm to 2 mm from the root of the anchor, respectively.

In one example, at least one of the second restraint portions is provided at one of the following positions of the fixing frame: the supporting section, a portion of the supporting body other than the supporting section, and the connecting portion.

In one example, at least one of the supporting sections further includes a bending section, the first restraint portion being provided on the bending section.

In one example, in a circumferential direction of the fixing frame, at least two adjacent supporting sections are connected in series by at least one of the restraint members.

In one example, the restraint member is provided with at least one buffer portion which is elastic and variable in length.

In one example, the first restraint portion is a first through hole and/or the second restraint portion is a second through hole, one end of the restraint member passes through the first through hole and/or the second through hole, and at least a portion of the restraint member is slidable within the first through hole and/or the second through hole.

According to the occlusion device, the supporting section is provided with at least one first restraint portion, the fixing frame is provided with at least one second restraint portion, and a restraint member is connected to the first restraint portion and the second restraint portion such that when a portion of the restraint member between the first restraint portion and the second restraint portion generates a restraint force, the restraint force restrains at least movement of the supporting section where the first restraint portion is located in a direction away from the fixing frame, thereby avoiding excessive outward opening of the supporting section.

DETAILED DESCRIPTION OF THE EMBODIMENTS

In order that the objects, solutions and advantages of the embodiments will be more clearly understood, the embodiments will be further described in detail hereinafter with reference to the accompanying drawings and examples. It should be understood that specific examples described herein are merely illustrative of the embodiments and are not intended to be limiting thereof.

It should be noted that in the field of intervention medical instruments, an end of a medical instrument implanted in a human or animal body that is closer to an operator is generally referred to as a "proximal end", an end that is further away from the operator is referred to as a "distal end", and the "proximal end" and "distal end" of any component of the medical instrument are defined in accordance with this principle. An "axial direction" generally refers to a longitudinal direction of the medical instrument when being delivered, and a "radial direction" generally refers to a direction of the medical instrument perpendicular to the "axial direction" thereof, and the "axial direction" and "radial direction" of any component of the medical instrument are defined in accordance with this principle.

The solutions of the embodiments will be described in further detail hereinafter with reference to specific examples. An occlusion device of the embodiments may be implanted into a body tissue of a human or animal body having an opening for occlusion of the opening, and is applied to, but not limited to, left atrial appendage occlusion and aneurysm occlusion.

Example 1

Figure 1:
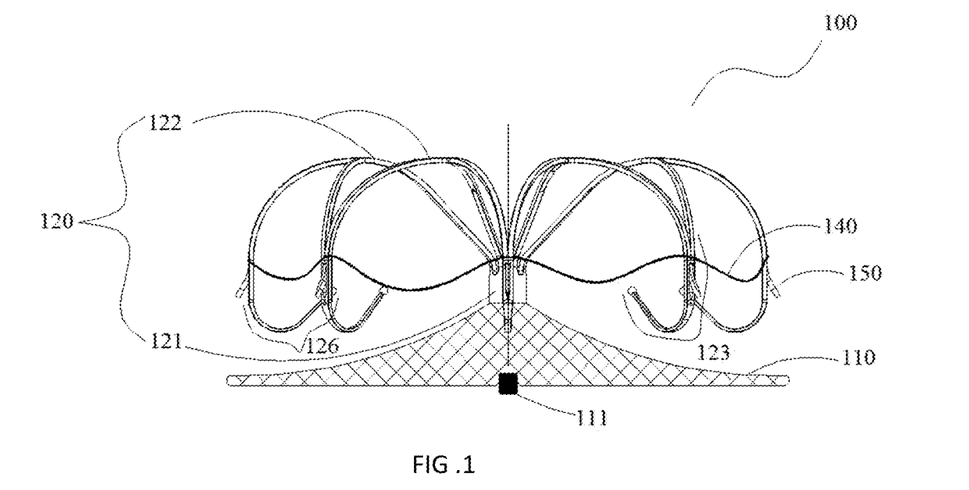
FIG. 1 is a schematic diagram of an external structure of an occlusion device of Example 1.
Figure 2:
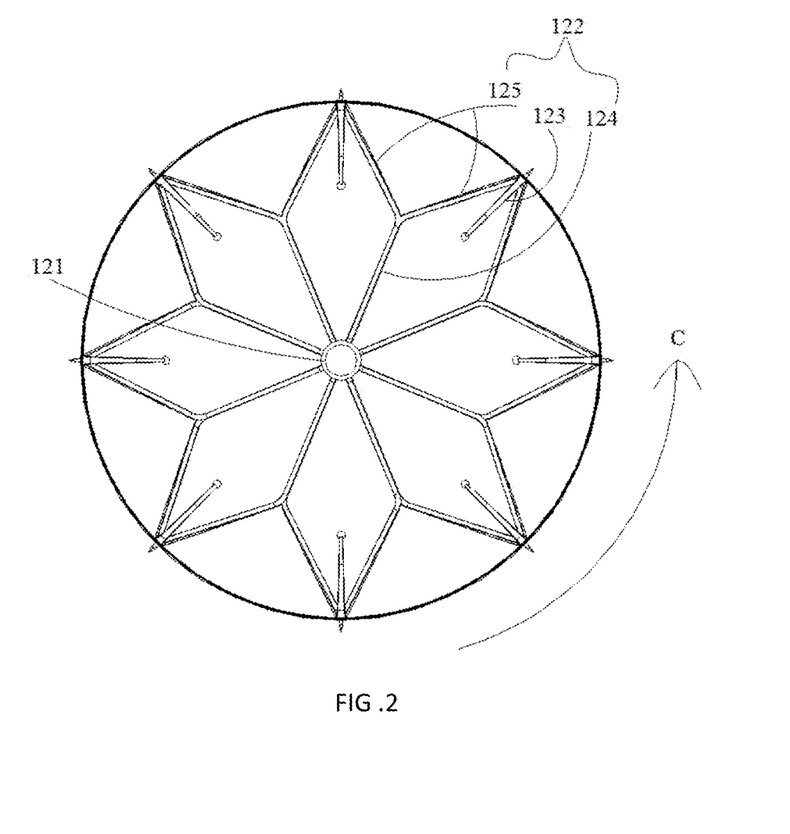
FIG. 2 is a schematic structural diagram of a fixing frame of the occlusion device of FIG. 1 as viewed from a proximal end to a distal end.

Example 1 provides an occlusion device 100 which, with reference to FIGS. 1 and 2 together, includes an elastic sealing disc 110 and an elastic fixing frame 120 connected to the sealing disc 110 and located on one side of the sealing disc 110. The sealing disc 110 and the fixing frame 120 are connectable directly or via at least one connecting member. The connecting member may be a flexible or rigid connecting member, which may be connected to one end of each of the sealing disc 110 and the fixing frame 120 by means of sleeving connection or welding, etc. In the present example, the sealing disc 110 is directly connected to the fixing frame 120. For example, a distal end of the sealing disc 110 extends into a connecting portion 121 at a proximal end of the fixing frame 120 and is fixed.

The sealing disc 110 may be formed of at least one metal wire having super-elasticity and shape memorability (e.g., nickel-titanium alloy wire) or biocompatible polymer wire, which is woven into a mesh tube, and both ends of the mesh tube are respectively closed and fixed by sleeves 111 and then heat-set into a flat shape or a disc shape or the like. The shape is not limited, as long as a tissue opening can be sealed after implantation. The sleeve 111 at a proximal end of the sealing disc 110 may not only sleeve a proximal end of the metal wire, but may also be removably connected, e.g., threaded, to a distal end of a delivery device for delivering the occlusion device 100. A sleeve (not shown) at a distal end of the sealing disc 110 is used not only for sleeving a distal end of the metal wire, but also for connection to the proximal end of the fixing frame 120 as well. At least one film body (not shown) is provided inside the sealing disc 110 to enhance the sealing performance of the sealing disc 110. The film body may be a PET film or another high polymer film, and the sealing disc 110 provided with the film body can prevent blood flow from passing through the sealing disc 110 from one side of the sealing disc 110 to the other side.

In another example, the sealing disc 110 may also be formed of at least one metal tube having super-elasticity and shape memorability, such as a nickel-titanium alloy tube, which is laser-cut and heat-set to a flat shape or a disc shape or the like. The shape is not limited, as long as a tissue opening can be sealed after implantation. In another example, the sealing disc 110 may also be formed of at least one metal rod having super-elasticity and shape memorability in a disc shape or the like. The shape is not limited, as long as a tissue opening can be sealed after implantation.

The fixing frame 120 includes a connecting portion 121 connected to the sealing disc 110, and a plurality of supporting bodies 122. The connecting portion 121 may be a nickel-titanium alloy tube having a hollow interior or may be woven from at least one nickel-titanium metal wire to form a tubular member having a hollow interior. The plurality of supporting bodies 122 radiate from a distal end of the connecting portion 121 to a distal end and cooperate to form a recessed area. The supporting bodies 122 are bent to extend towards a proximal end and form a plurality of spaced-apart suspending supporting sections 123, tail ends of the plurality of supporting sections 123 enclosing a proximal opening. The suspending supporting section 123 may be formed by a suspending portion of one end of the single supporting body 122 which is not connected to the connecting portion 121 or may be formed by suspending portions of more than two supporting bodies 122 which are gathered together and may also be formed by suspending portions of more than two supporting bodies 122 which are crossed together.

In the present example, the supporting section 123 is formed by the suspending portions of two supporting bodies 122 which are gathered together in FIG. 1. Specifically, referring to FIG. 2, a portion of each supporting body 122 other than the supporting section 123 thereof includes a lead-out section 124 connected to the connecting portion 121 and two branch sections 125 located between the lead-out section 124 and the supporting section 123. One branch section 125 of one supporting body 122 and the other branch section 125 closest to the branch section 125 of another supporting body 122 adjacent to the supporting body 122 are gathered at the proximal end to form one supporting section 123. The suspending supporting sections 123 are spaced apart in a circumferential direction C of the fixing frame 120. In actual production, a plurality of supporting bodies 122 may be cut from one end of a nickel-titanium alloy tube in a direction toward the other end, and then each supporting body 122 is opened by a mold and heat-set. An uncut portion of the nickel-titanium alloy tube is the connecting portion 121.

In other examples, the supporting body 122 may be also formed of at least one metal wire having super-elasticity and shape memorability (e.g., nickel-titanium wire). For example, the supporting body 122 may be a single nickel-titanium wire or may also be formed of more than two metal wires which are wound or woven. One end of the plurality of supporting bodies 122 is connected to the connecting portion 121 and the remaining portions are shaped like an umbrella by heat setting, thereby obtaining the fixing frame 120 having a distal recessed area and a proximal opening.

In other examples, the fixing frame 120 may include a connecting portion 121 and a supporting body 122 connected to the connecting portion 121. The fixing frame 120 having the distal recessed area and the proximal opening may be obtained by cutting an elastic material in a trumpet shape or a tube shape and then heat-setting into an umbrella shape. The connecting portion 121 is located at an end with a smaller outer diameter of the elastic material, a portion of the elastic material other than the connecting portion 121 is the supporting body 122, the supporting body 122 occupies most of the elastic material, and the cut suspending portion is the supporting section 123. A wall of the supporting body 122 may or may not be provided with a plurality of uniformly distributed openings.

In other examples, at least one supporting body 122 radiates from the connecting portion 121 and extends towards a proximal end, may not form a recessed area on the fixing frame 120 as in the present example, e.g., may radiate in parallel from a distal end of the connecting portion 121, bend outwards and extend towards a proximal end, as well as forming a plurality of spaced-apart suspending supporting sections 123. Here, the particular case in which at least one supporting body 122 radiates from the connecting portion 121 is not listed any more, as long as a plurality of spaced-apart suspending supporting sections 123 can be formed after extending towards the proximal end.

Figure 3:
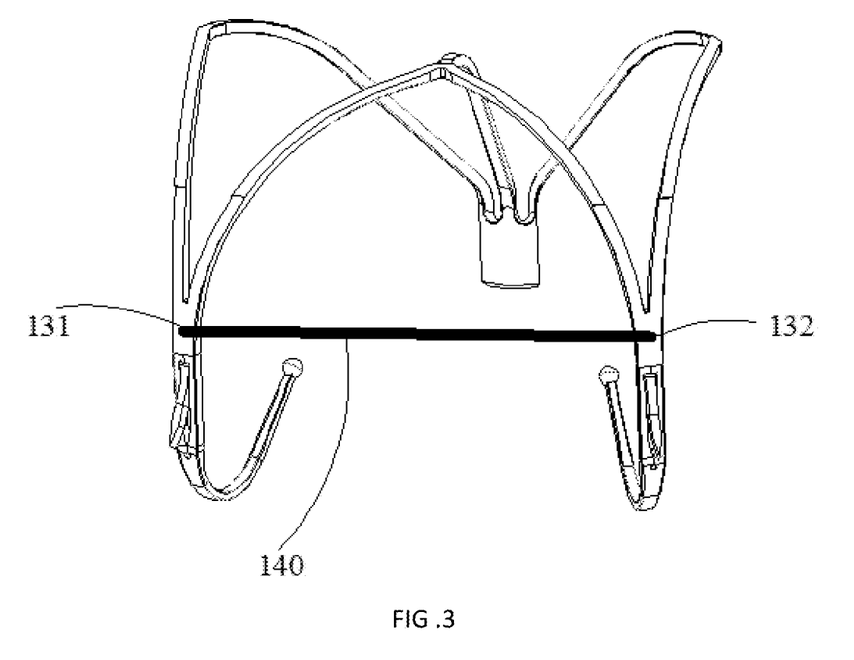
FIG. 3 is a schematic diagram of a partial structure of the fixing frame of the occlusion device of FIG. 1.

In the present example, referring to FIGS. 1 and 3 together, the fixing frame 120 is provided with a plurality of first restraint portions 131 and a plurality of second restraint portions 132. The first restraint portions 131 and the second restraint portions 132 are provided on different supporting sections 123, respectively, and only one first restraint portion 131 or one second restraint portion 132 is provided on one supporting section 123. That is, the supporting body 122 provided with the first restraint portion 131 and the supporting body 122 provided with the second restraint portion 132 are not the same supporting body 122. The first restraint portions 131 and the second restraint portions 132 are sequentially distributed at intervals in the circumferential direction C of the fixing frame 120, all the first restraint portions 131 and all the second restraint portions 132 are connected through one restraint member 140, and all the supporting sections 123 are connected in series through the restraint member 140 in the circumferential direction C of the fixing frame 120, so that the restraint member 140 is connected to the first restraint portions 131 and the second restraint portions 132 in series. It may be noted that the first restraint portion 131 and the second restraint portion 132 may be restraint positions defined on the fixing frame 120 by a restraint force of the restraint member 140. For example, the restraint member 140 may be connected to the two restraint positions namely the first restraint portion 131 and the second restraint portion 132 in such a manner as to be bound, welded, bonded, etc. The first restraint portion 131 and the second restraint portion 132 may also be a solid structure defined on the fixing frame 120. For example, the first restraint portion 131 may be a through hole, a raised structure, a groove structure, etc., and the restraint member 140 may be connected to the solid structures of the first restraint portion 131 and the second restraint portion 132, so that the first restraint portion 131 and the second restraint portion 132 are applied with a restraint force through the corresponding solid structures, and the connection to the corresponding solid structures may be penetration into the through hole, may be binding with the raised structure and may be binding with the groove structure, etc. which will not be described in detail here.

In the present example, after the restraint member 140 is connected to the first restraint portion 131 and the second restraint portion 132, the restraint member 140 pulls between the first restraint portion 131 and the second restraint portion 132, so that at least a portion of the restraint member 140 between the first restraint portion 131 and the second restraint portion 132 generates a restraint force. It may be noted that in the natural state, i.e., when the fixing frame 120 is not subjected to an external force other than gravity after being released, the restraint member 140 is in a stretched state. At this moment, at least the portion of the restraint member 140 between the first restraint portion 131 and the second restraint portion 132 has a certain restraint force. In this example, the first restraint portion 131 and the second restraint portion 132 are provided on different supporting sections 123, respectively, so that the restraint force generated by this portion of the restraint member 140 may exert a restraint effect not only on the supporting section 123 where the first restraint portion 131 is located, but also on the connected supporting section 123 where the second restraint portion 132 is located. The supporting sections 123 provided with the first restraint portion 131 and the second restraint portion 132 may be restrained from moving away from the fixing frame 120 by the restraint force generated on the restraint member 140.

It may be understood that all of the first restraint portions 131 and all of the second restraint portions 132 may be connected by two or more restraint members 140, and all of the supporting sections 123 are connected in series by two or more restraint members 140 in the circumferential direction C of the fixing frame 120.

In other examples, each supporting section 123 may be provided with two or more first restraint portions 131 or second restraint portions 132 and may also be provided with two or more restraint members 140, thereby increasing the connection strength between the supporting bodies 122 and the restraint members 140. By way of example of providing two restraint members 140 and two first restraint portions 131 or second restraint portions 132 on each supporting section 123 spaced apart in an axial direction of the supporting section 123, a plurality of first restraint portions 131 and a plurality of second restraint portions 132 near the tail end of the supporting section 123 may be sequentially connected in the circumferential direction C of the fixing frame 120 by one restraint member 140, and a plurality of first restraint portions 131 and a plurality of second restraint portions 132 near the distal end of the supporting section 123 may be sequentially connected in the circumferential direction C of the fixing frame 120 by another restraint member 140. The two restraint members 140 do not cross each other in the axial direction of the supporting section 123 and may, in some cases, be provided in approximately parallel.

Figure 4:
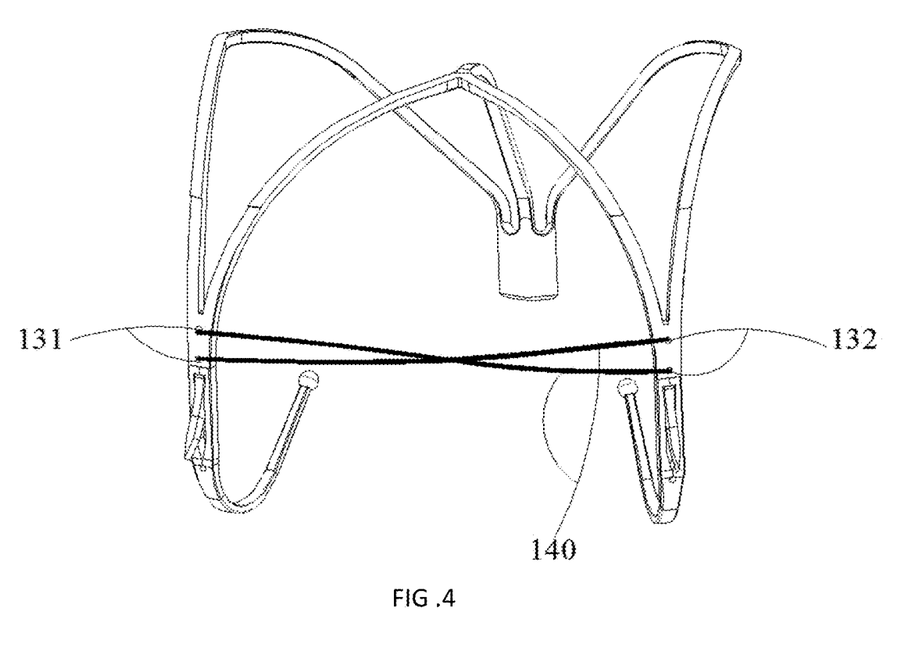
FIG. 4 is a schematic diagram of another partial structure of the fixing frame of the occlusion device of Example 1.

In other examples, referring to FIG. 4, the two restraint members 140 may connect the first restraint portions 131 and the second restraint portions 132 in a crossed manner in the circumferential direction C of the fixing frame 120. In other examples, a plurality of restraint members 140 may be provided and at least one first restraint portion 131, and at least one second restraint portion 132 on two or more supporting sections 123 adjacent in the circumferential direction C of the fixing frame 120 may be connected by at least one restraint member 140. Other arrangements, similar to these instances, may be implemented to restrain movement of all of the supporting sections 123 on the fixing frame 120 in a direction away from the fixing frame 120, and will not be listed here.

In the present example, each supporting section 123 is provided with an anchor 150 facing the sealing disc 110, a root of the anchor 150 is fixedly connected to the supporting section 123, and each of the first restraint portions 131 and each of the second restraint portions 132 are both provided near one of the anchors 150 corresponding thereto, for example, at a position closer to the distal end of the supporting section 123 than the root of the anchor 150 as shown in FIG. 1. It may be desired that the supporting section 123 is located on the root of the anchor within a range of 0.1 mm to 2 mm, the restraint to the radial movement of the supporting section 123 is more effective, and the restraint to the radial direction of all the supporting sections 123 of the fixing frame 120 as a whole is more stable.

In other examples, the first restraint portion 131 and/or the second restraint portion 132 may each be an opening in the supporting body 122 that is left after the anchor 150 has been cut to avoid reducing the supporting strength of the supporting section 123. In other examples, a portion of the supporting sections 123 of the fixing frame 120 may be provided with at least one anchor 150 facing the sealing disc 110, respectively, and at least one first restraint portion 131 and/or at least one second restraint portion 132 may be provided near at least one anchor 150 corresponding thereto, respectively, to achieve a better radial restraint to the portion of the supporting sections 123. In other examples, the fixing frame 120 may not be provided with an anchor 150, and after being released within a cavity, the fixing frame 120 may provide support for the occlusion device 100 to fix at least a portion of the occlusion device 100 within the cavity of the left atrial appendage.

Figure 5:
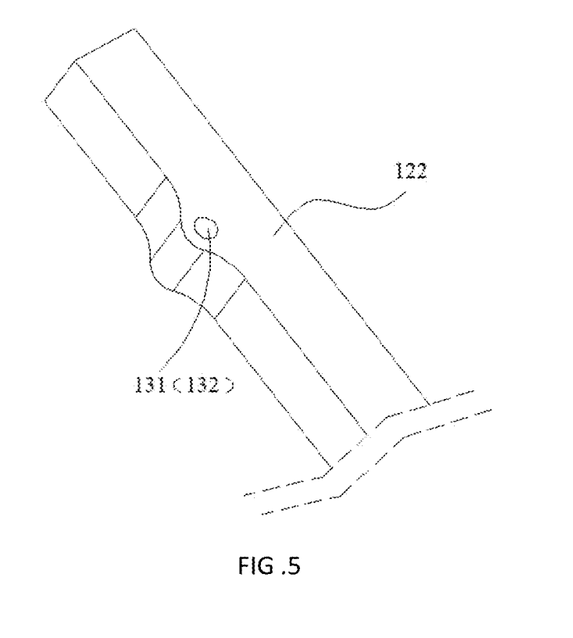
FIG. 5 is another schematic structural diagram of a first restraint portion or a second restraint portion provided on a supporting body in the occlusion device of Example 1.

In the present example, the first restraint portion 131 and the second restraint portion 132 are each a through hole provided in the fixing frame 120 and may be formed by perforating the fixing frame 120. In this example, the restraint member 140 may pass through the through hole (i.e., the first restraint portion 131 or the second restraint portion 132), thereby connecting the first restraint portion 131 and the second restraint portion 132. One end or a portion of the restraint member 140 is connected to the first restraint portion 131 or the second restraint portion 132 on the supporting body 122 in such a manner as to be knotted or wound after passing through the through hole, or one end of the restraint member 140 is heat-fused into a ball shape after passing through the through hole, and at least a portion of the restraint member 140 having a ball-shaped tail end is slidable within the through hole. In other examples, the through hole provided on the supporting body 122 is located on the central axis of the supporting body 122, and since the position of the through hole is relatively centered, a metal rod at the position of the through hole is relatively not too weak to be easily broken. In other examples, referring to FIG. 5, the through hole (i.e. the first restraint portion 131 or the second restraint portion 132) provided in the supporting body 122 is located at a side edge of the supporting body 122, and an outer diameter of a portion of the supporting body 122 where the through hole is provided is larger than an outer diameter of a portion where the through hole is not provided, so that the portion where the through hole is provided still has sufficient supporting strength and is not easily broken. The specific form of the through hole is not limited, and may be provided as a circular hole or an elliptical hole, or may be an elongated hole provided in the axial direction of the supporting body 122.

Figure 6:
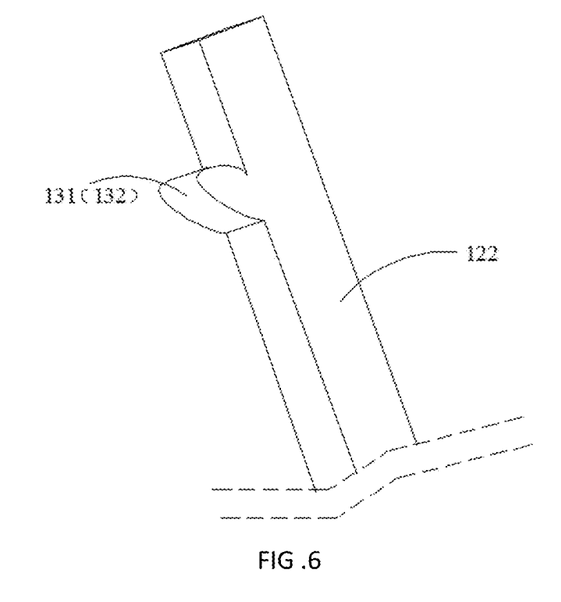
FIG. 6 is another schematic structural diagram of the first restraint portion or the second restraint portion provided on the supporting body in the occlusion device of Example 1.
Figure 7:
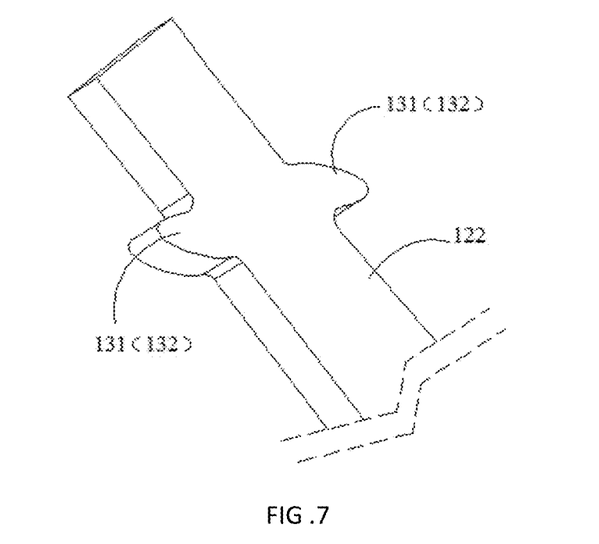
FIG. 7 is another schematic structural diagram of the first restraint portion or the second restraint portion provided on the supporting body in the occlusion device of Example 1.
Figure 8:
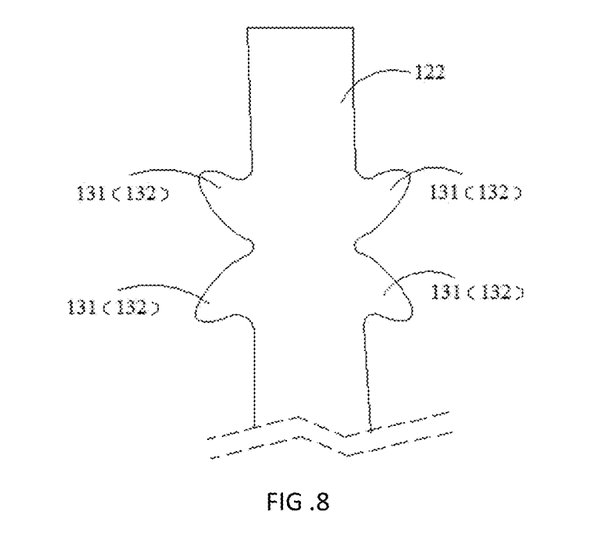
FIG. 8 is another schematic structural diagram of the first restraint portion or the second restraint portion provided on the supporting body in the occlusion device of Example 1.

The elongated through hole has a larger length and a smaller width in the axial direction of the supporting body 122, so that the supporting strength of the portion of the supporting body 122 where the through hole is provided is not excessively affected. In addition, the restraint member 140 matching the through hole has a certain degree of freedom in the axial direction of the supporting body 122, so that when the fixing frame 120 enters or exits from a sheath, the length of the restraint member 140 between the first restraint portion 131 and the second restraint portion 132 may vary in accordance with the deformation of the supporting body 122 while ensuring that the radial movement of the supporting section 123 is properly restrained. In other examples, referring to FIGS. 6-8, the first restraint portion 131 may also be at least one projection provided on the fixing frame 120 and the second restraint portion 132 may also be at least one projection provided on the fixing frame 120. In this example, the restraint member 140 may be wrapped around the projection (i.e., the first restraint portion 131 or the second restraint portion 132) to connect the first restraint portion 131 and the second restraint portion 132. The specific manner of connecting one end or a portion of the restraint member 140 to the first restraint portion 131 or the second restraint portion 132 on the supporting body 122 may be binding, welding or bonding to the projection. The shape of the projection is not limited, and may be circular or other irregular shapes, for example unpointed or non-pointed shapes. The projection may be of an imporous or non-porous structure or may be of an annular porous structure (similar to that shown in FIG. 5). Various combinations of the specific forms of the first restraint portion 131 and the second restraint portion 132 are not described in detail herein.

The restraint member 140 in the present example is made of at least a thread-like member. The thread-like member may be made of a high polymer material such as a PET polyester thread, a PP suture thread and a PA suture thread, and may be made of a metal material such as nickel-titanium and stainless steel.

In other examples, the first restraint portion 131 may also be provided on a portion of one supporting body 122 adjacent to the supporting section 123 other than the supporting section 123, such as on the branch section 125. As the arrangement position is closer to the distal end of the supporting section 123, the restraint effect is better. In other examples, the second restraint portion 132 may also be provided on a portion of one supporting body 122 other than the supporting section 123 (e.g., the lead-out section 124 or the branch section 125), or the connecting portion 121 of the fixing frame 120 or the like. The specific combinations of the arrangement position of the first restraint portion 131 and the arrangement position of the matching second restraint portion 132 are not listed here one by one, so long as at least one first restraint portion 131 and at least one second restraint portion 132 matching the first restraint portion 131 may be connected through at least one restraint member 140, so as to restrain the movement of at least one supporting section 123 corresponding to the first restraint portions 131 and the second restraint portions 132 in a direction away from the fixing frame 120.

In the present example, each supporting section 123 also includes a bending section 126. The bending section 126 is formed by bending the tail end of the supporting section 123 towards the interior of the occlusion device 100 to reduce friction or damage to tissue in the body caused by the tail end of the supporting section 123. In other examples, the supporting section 123 of the fixing frame 120 is not provided with the bending section 126 or only a portion of the supporting section 123 of the fixing frame 120 includes the bending section 126.

In other examples, at least one restraint member 140 may be provided with at least one buffer portion which is elastic and variable in length. The buffer portion may have a spiral line shape or a wavy line shape, and the specific shape is not limited. The buffer portion can ensure that the restraint member 140 does not influence the conversion of the fixing frame 120 between a folded state and an unfolded state, thereby ensuring the delivery and normal use of the occlusion device 100.

The occlusion device 100 in any of the above examples, when delivered from the exterior of the body to the interior of the body, is restrained to be approximately linear by the cavity of a delivery device such as a sheath, so as to be in a folded state. Taking the sheath as an example, when the sheath is released in the body, the sheath is withdrawn towards the proximal end, so that the fixing frame 120 at the distal end first extends from the cavity of the sheath, the distal end of each supporting body 122 on the fixing frame 120 is radially opened outwards and then bent towards the proximal end, and as the proximal end portion of the fixing frame 120 is released from the interior of the sheath, it continues to extend towards the proximal end until it returns to a heat-set state, thereby being in an unfolded state. The released fixing frame 120 may be fixed to an inner wall of a body tissue having a cavity, such as the left atrial appendage, to fix the occlusion device 100 to the body tissue. Thereafter, the sheath is further withdrawn towards the proximal end, and the sealing disc 110 extending from the cavity of the sheath is unfolded to a flat or disc shape after heat-setting, thereby covering an opening of a portion to be sealed, and smoothly achieving sealing.

Example 2

The same portion of an occlusion device 200 of Example 2 as that of the occlusion device 100 of Example 1 will not be described in detail here, and the difference therebetween is mainly that in Example 2, in a circumferential direction C of a fixing frame, at least two adjacent supporting sections are connected in series by at least one restraint member. For example, referring to FIG. 9, only some supporting sections 223 on a fixing frame 220 are provided with a first restraint portion 231 or a second restraint portion 232, respectively, and the first restraint portion 231 and the second restraint portion 232 matching therewith are provided on two adjacent supporting sections 223 in the circumferential direction C of the fixing frame 220, respectively. A plurality of restraint members 240 are spaced apart dispersedly in the circumferential direction C of the fixing frame 220 instead of being arranged consecutively in Example 1. Such an occlusion device 200 achieves the restraint of radial movement of some of the supporting sections 223 of the fixing frame 220 to avoid excessive outward opening of the supporting sections 223.

Figure 9:
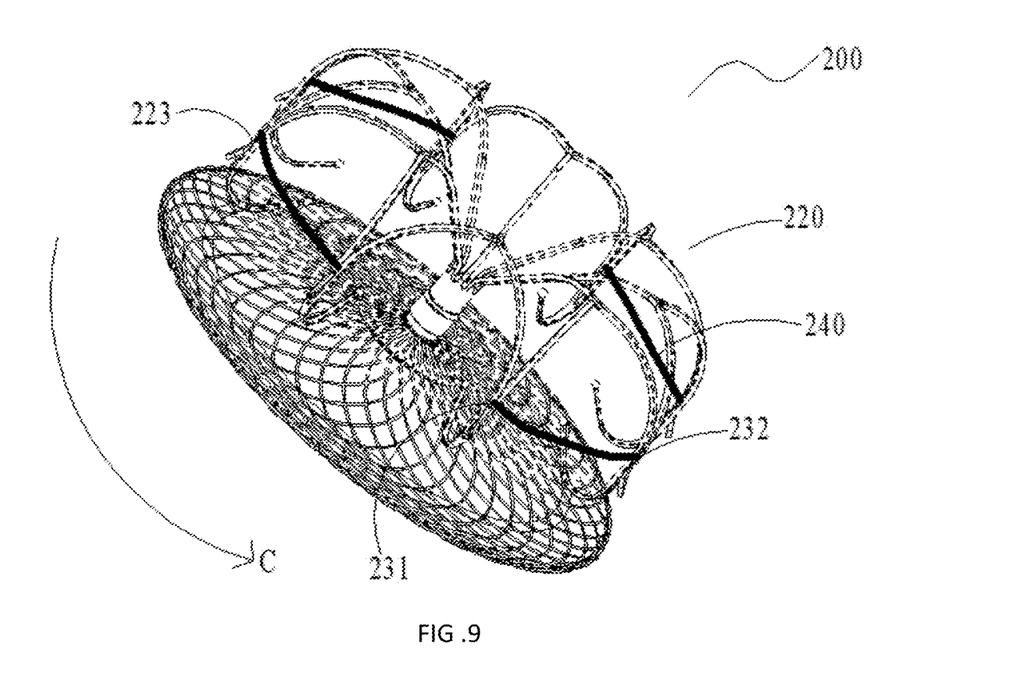
FIG. 9 is a schematic structural diagram of an occlusion device of Example 2.

In other examples, at least one first restraint portion 231 or at least one second restraint portion 232 may be provided in the circumferential direction C of the fixing frame 220 at three or more adjacent supporting sections 223 or other portions of the supporting body near the distal end thereof, respectively, and a plurality of restraint members 240 may be spaced apart dispersedly in the circumferential direction C of the fixing frame 220 after being fixed to the fixing frame 220. Such an arrangement also achieves the restraint of radial movement of some of the supporting sections 223 of the fixing frame 220 to avoid excessive outward opening of the supporting sections 223.

Example 3

Figure 10:
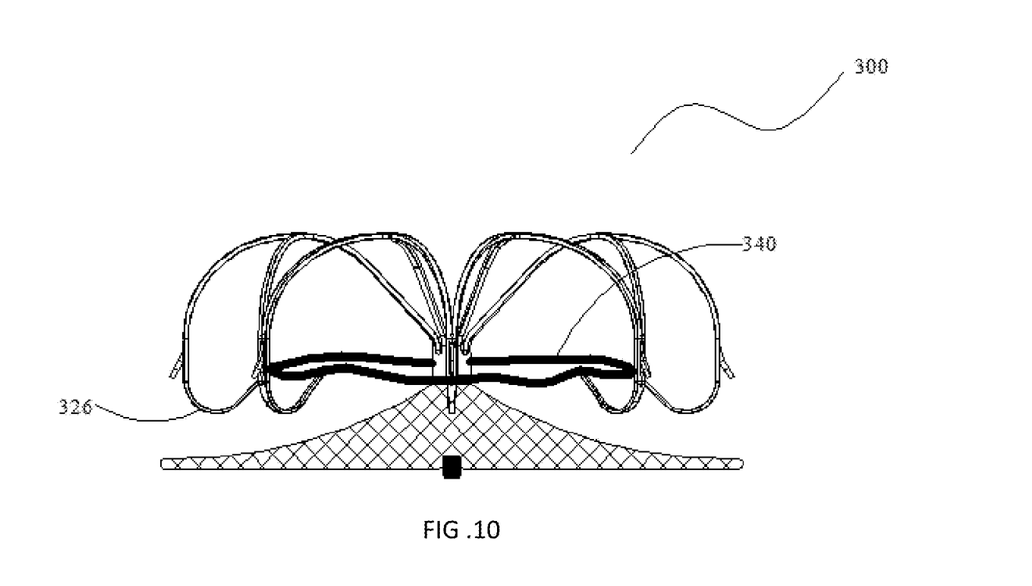
FIG. 10 is a schematic structural diagram of an occlusion device of Example 3.

The same portion of an occlusion device 300 of Example 3 as that of the occlusion device 100 of Example 1 will not be described in detail here, and the difference therebetween is mainly that in Example 3, a first restraint portion and a second restraint portion are provided at any positions of a bending section, respectively. Further, the first restraint portion and the second restraint portion are provided at the tail end of the bending section, respectively. For example, a hole may be punched at the tail end of the bending section, or at least one projection may be provided at the tail end of the bending section, as long as one end or a portion of the restraint member can be fixed at the tail end of the supporting section.

For example, referring to FIG. 10, the tail end of the bending section 326 is provided with a ball (not shown), which may be implemented by heat-fusing the tail end of the bending section 326 or by fixedly connecting a ball to the tail end of the bending section 326. The ball is provided with a through hole which at least one end or a portion of restraint member 340 passes to fix the restraint member 340 to the tail end of the supporting section by knotting or heat-fusing the tail end, or winding, etc. Such an arrangement uses less material for the restraint member 340 and greater radial restraint between the various supporting sections.

It may be understood that the provision of a plurality of first restraint portions and a plurality of second restraint portions at the tail ends of the bending sections 326 and the structural features of at least one restraint member 340 in Example 2 may be added to the occlusion device 100 of Example 1 to further enhance the effect of restraining the movement of the plurality of supporting sections of the fixing frame in a direction away from the fixing frame.

Example 4

The same portion of the occlusion device of Example 4 as that of the occlusion device 100 of Example 1 will not be described in detail here, and the difference therebetween is mainly that in Example 4, a supporting body provided with a first restraint portion is the same as a supporting body provided with a second restraint portion. For example, referring to FIG. 11, a fixing frame 420 is provided with a first restraint portion 431 on a supporting section 423 of each supporting body 422. For each first restraint portion 431, a second restraint portion 432 is provided at a position of the supporting body 422 close to a connecting portion 421 where the first restraint portion 431 is located, thereby restraining the movement of all the supporting sections 423 of the fixing frame 420 in a direction away from the fixing frame 420.

Figure 11:
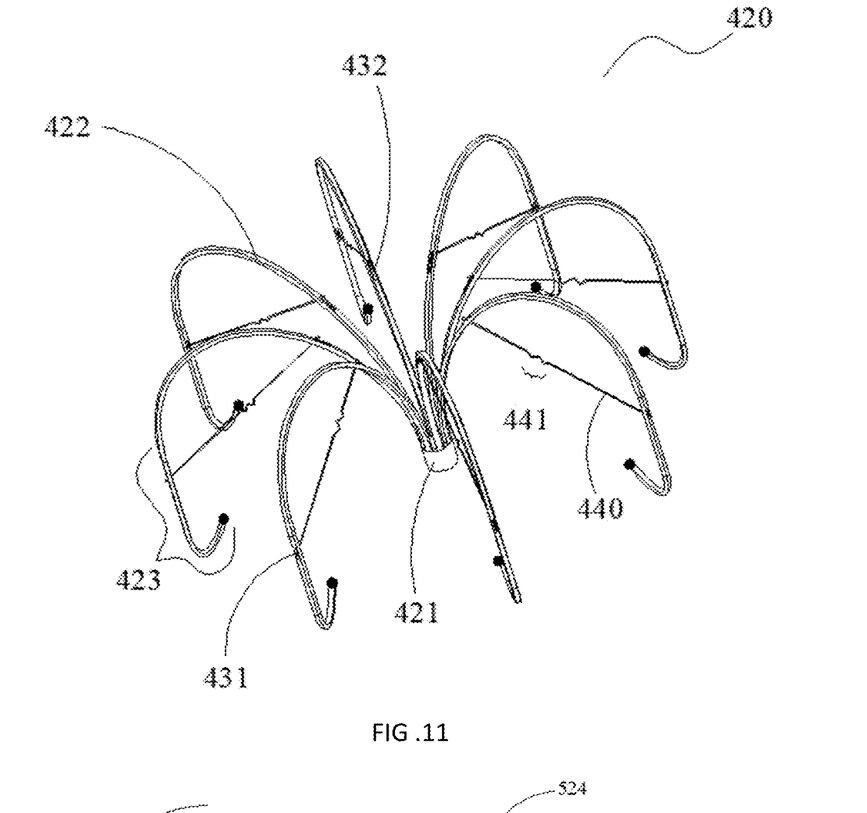
FIG. 11 is a schematic structural diagram of a fixing frame of an occlusion device of Example 4.

At least one restraint member 440 is provided with at least one buffer portion 441. The buffer portion 441 is elastic and variable in length. The buffer portion 441 may have a spiral line shape or a wavy line shape, and the specific shape is not limited. The buffer portion 441 can ensure that a restraint member 440 does not influence the conversion of the fixing frame 420 between a folded state and an unfolded state, thereby ensuring the delivery and normal use of the occlusion device. In other examples, the buffer portion 441 may be eliminated, the length of the restraint member 440 may be adjusted, etc. without affecting the conversion of the fixing frame 420 between the folded state and the unfolded state.

In other examples, the fixing frame 420 may be provided with at least one first restraint portion 431 on only one or a portion of the plurality of supporting bodies 422, respectively, and at least one second restraint portion 432 on the respective supporting body 422 or connecting portions 421 respectively. For example, at least one first restraint portion 431 is provided on the supporting section 423 of the same supporting body 422, and at least one second restraint portion 432 is provided on the supporting body 422 at a position close to the connecting portion 421 so as to restrain the radial movement of the individual supporting section 423 and avoid excessive outward opening of the supporting section 423. The arrangement on two or more supporting bodies 422 is similar and will not be listed here.

Example 5

Figure 12:
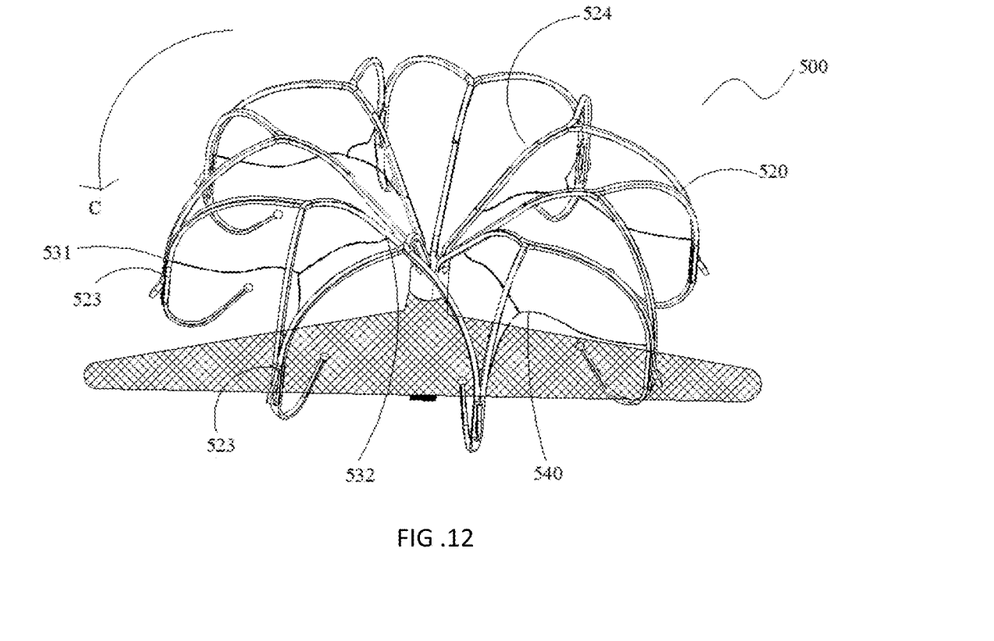
FIG. 12 is a schematic structural diagram of an occlusion device of Example 5, where a fixing frame of the occlusion device is bent towards one side for convenience of observation.

The same portion of an occlusion device 500 of Example 5 as that of the occlusion device 100 of Example 1 will not be described in detail here, and the difference therebetween is mainly that in Example 5, at least two supporting sections adjacent in a circumferential direction C of a fixing frame are connected to a portion of the same supporting body other than the supporting sections thereof through at least one restraint member.

For example, referring to FIG. 12, each group of two adjacent supporting sections 523 in a circumferential direction C of a fixing frame 520 is provided with a first restraint portion 531 respectively, a second restraint portion 532 is provided on a lead-out section 524 between the two supporting sections 523, a restraint member 540 is radial and has three tail ends, and each tail end of the restraint member 540 is connected to the two first restraint portions 531 and the second restraint portion 532 respectively, thereby restraining the movement of all the supporting sections 523 of the fixing frame 520 in a direction away from the fixing frame 520.

In other examples, a plurality of groups of supporting sections 523 adjacent to each other in the circumferential direction C of the fixing frame 520 may be provided with first restraint portions 531 respectively, each group of supporting sections 523 includes two or more supporting sections 523, and the supporting sections 523 of the same group are connected to the same lead-out section 524 or to at least two lead-out sections 524 or to a connecting portion.

Example 6

Figure 13:
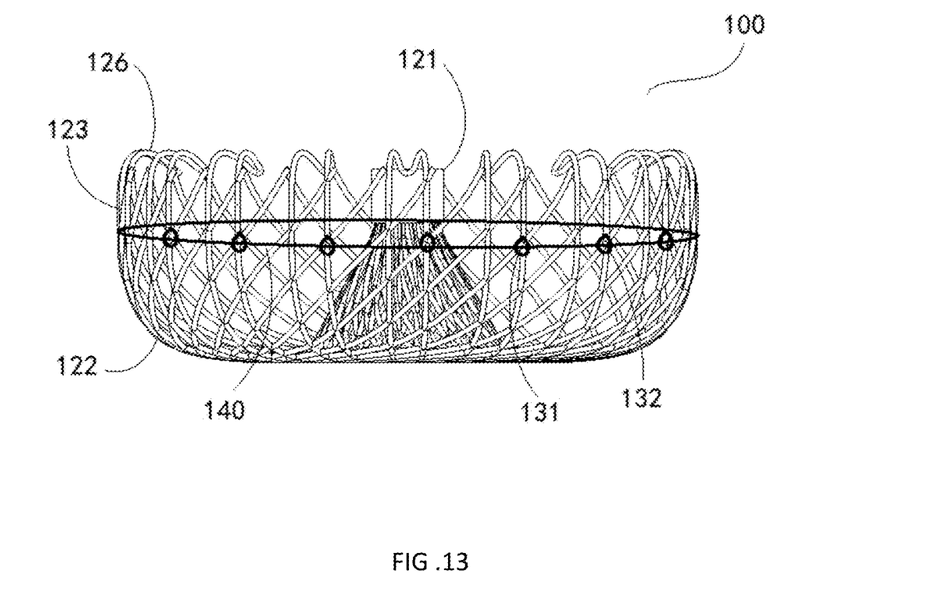
FIG. 13 is a schematic structural diagram of a fixing frame of an occlusion device of Example 6.
Figure 14:
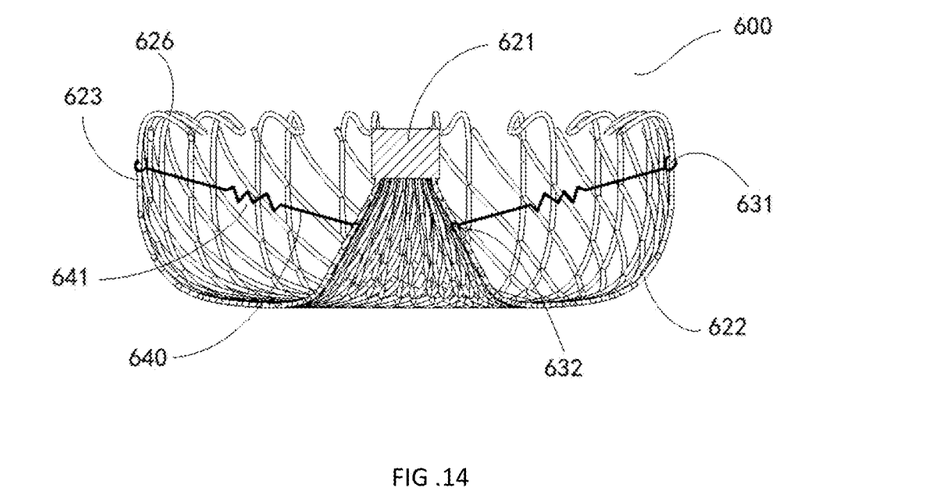
FIG. 14 is another schematic structural diagram of the fixing frame of the occlusion device of Example 6.

The same portion of the occlusion device of Example 6 as that of the occlusion device of any of the above examples will not be described in detail here, and the difference therebetween is mainly that in Example 6, a fixing frame 600 includes a structure in which at least one supporting body 622 is woven and then heat-set into an umbrella shape, and a connecting portion 621 provided at one end of the umbrella-shaped structure and connected to a sealing disc. As shown in FIGS. 13 and 14, in the present example, the supporting body 622 may be a nickel-titanium metal wire having super-elasticity and shape memorability, and the connecting portion 621 may be a metal sleeve capable of restraining the metal wire. A portion of the supporting body 622 between distal and proximal ends of the fixing frame 600 is a supporting section 623, and one supporting body 622 includes at least one supporting section 623. The tail end of the supporting section 623 is bent into the fixing frame 600 to form a bending section 626. A plurality of supporting sections 623 have such bending sections, and each supporting section 623 may be provided with a bending section 626 respectively. The tail ends of two or more adjacent bending sections 626 in the circumferential direction of the fixing frame 600 may be fixedly connected. For example, in FIG. 13, the tail ends of two adjacent bending sections 626 are fixedly connected to form a V-shaped bending portion. The function of the V-shaped bending portion is the same as the function of the bending section in any of the above examples. The V-shaped bending portion in FIG. 13 may in practice be made from the same supporting body 622 by weaving.

The plurality of supporting bodies 622 are provided with a first restraint portion 631 and a second restraint portion 632 which are the same as any of the above examples respectively to fix the restraint member 640 to the fixing frame 600. For example, in FIG. 13, at least one restraint member 640 is fixed to each supporting section 623 in the circumferential direction of the fixing frame by repeated winding or binding. In other examples, the first restraint portion 631 and the second restraint portion 632 may be identical or similar in specific structure, arrangement position and connection manner to any of the above examples and will not be described in detail herein. The restraint member 640 is also the same as the restraint member in any of the above examples, e.g., the restraint member 640 is a wire member. The restraint member 640 may also be provided with a buffer portion 641 similar to any of the above examples. The various features of the above examples and embodiments may be combined in any manner, and in order to simplify the description, all possible combinations of the various features in the above examples are not described. However, as long as the combinations of these features are not contradictory, they should be considered to be within the scope of the embodiments.

The above examples express only a few embodiments, which are described in greater detail but are not to be construed as limiting. It will be appreciated by those of ordinary skill in the art that numerous variations and modifications may be made to the embodiments without departing from the scope of the embodiments.

The invention claimed is:

1. An occlusion device, comprising:
  a sealing disc, and a fixing frame connected to the sealing disc and located on one side of the sealing disc, the fixing frame comprising a connecting portion connected to the sealing disc and at least one supporting body, the at least one supporting body radiating from the connecting portion and extending towards a proximal end to form a plurality of supporting sections, wherein each supporting section is provided with at least one first restraint portion or at least one second restraint portion;

the occlusion device further comprising at least one restraint member which is connected to the at least one first restraint portion and the at least one second restraint portion such that when a portion of the at least one restraint member between the at least one first restraint portion and the at least one second restraint portion generates a restraint force, the restraint force at least restrains movement of the plurality of supporting sections where the at least one first restraint portion or the at least one second restraint portion is located in a direction away from the fixing frame;

the at least one restraint member is a thread-like member, wherein, the at least one first restraint portion is positioned adjacent to the at least one second restraint portion in a circumferential direction of the fixing frame, and the at least one restraint member is located between the at least one first restraint portion and the at least one second restraint portion in the circumferential direction of the fixing frame.

2. The occlusion device according to claim 1, wherein a supporting section of the plurality of supporting sections provided with the at least one first restraint portion is the same as or different from a supporting section of the plurality of supporting sections provided with the at least one second restraint portion.

3. The occlusion device according to claim 2, wherein the at least one first restraint portion and the at least one second restraint portion are provided on different supporting sections, respectively.

4. The occlusion device according to claim 3, wherein at least one of the plurality of supporting sections is provided with at least one anchor towards the sealing disc, a root of the at least one anchor being fixedly connected to the at least one of the plurality of supporting sections, and the at least one first restraint portion and/or the at least one second restraint portion being provided on the at least one of the plurality of supporting sections within the range of 0.1 mm to 2 mm from the root of the at least one anchor, respectively.

5. The occlusion device according to claim 2, wherein the at least one second restraint portion is provided at one of the following positions of the fixing frame:
one supporting section of the plurality of supporting sections, a portion of the at least one supporting body other than the one supporting section of the plurality of supporting sections, and the connecting portion.

6. The occlusion device according to claim 1, wherein the at least one second restraint portion is provided at one of the following positions of the fixing frame: one supporting section of the plurality of supporting sections, a portion of the at least one supporting body other than the one supporting section of the plurality of supporting sections, and the connecting portion.

7. The occlusion device according to claim 1, wherein at least one of the plurality of supporting sections further comprises a bending section.

8. The occlusion device according to claim 7, wherein the bending section is provided with a ball.

9. The occlusion device according to claim 8, wherein the ball is provided with a through hole which at least one end or a portion of the at least one restraint member passes through.

10. The occlusion device according to claim 1, wherein, in the circumferential direction of the fixing frame, at least two adjacent supporting sections of the plurality of supporting sections are connected in series by the at least one restraint member.

11. The occlusion device according to claim 1, wherein the at least one restraint member is provided with at least one buffer portion which is elastic and variable in length.

12. The occlusion device according to claim 11, wherein the at least one buffer portion has a spiral line shape or a wavy line shape.

13. The occlusion device according to claim 1, wherein the at least one first restraint portion is a first through hole and/or the at least one second restraint portion is a second through hole, one end of the at least one restraint member passes through the first through hole and/or the second through hole, and at least a portion of the at least one restraint member is slidable within the first through hole and/or the second through hole.

14. The occlusion device according to claim 13, wherein each through hole provided in the at least one supporting body is located at a side of the at least one supporting body, and an outer diameter of a portion of the at least one supporting body where the each through hole is provided is larger than an outer diameter of a portion where the each through hole is not provided.

15. The occlusion device according to claim 1, wherein one end of the at least one first restraint portion and the at least one second restraint portion is bent in the circumferential direction away from the sealing disc.

16. The occlusion device according to claim 1, wherein the sealing disc is located on a proximal side of the fixing frame.

17. The occlusion device according to claim 1, wherein, in the circumferential direction of the fixing frame, all of the supporting bodies define an opening towards the sealing disc.

18. The occlusion device according to claim 1, wherein all of the supporting bodies are configured to define an opening towards the sealing disc, and an end portion of the at least one supporting body, which is located closer to the sealing disc, is bent towards a side away from the sealing disc.

19. The occlusion device according to claim 1, wherein the at least one restraint member is made of polymer.

* * * * *